US00PP10383P

United States Patent [19]

Bos

[11] Patent Number: Plant 10,383

[45] Date of Patent: May 5, 1998

[54] GUZMANIA PLANT NAMED 'SUNSTAR'

[76] Inventor: Henny Bos, Hoefslag 1, 2641 ZZ Pijnacker, Netherlands

[21] Appl. No.: 767,212

[22] Filed: Dec. 16, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—C. A. Whealy

[57] ABSTRACT

A distinct cultivar of Guzmania plant named 'Sunstar', characterized by its young leaves that have green margins with dark pink centers and mature leaves that have green margins with light yellow centers.

1 Drawing Sheet

The present invention relates to a new and distinct cultivar of Guzmania plant, botanically known as *Guzmania lingulata*, and hereinafter referred to by the cultivar name 'Sunstar'.

The new cultivar was discovered in 1982 by the inventor in Pijnacker, The Netherlands, in a controlled environment as a naturally occurring mutation in a large population of plants of the cultivar 'Remembrance' (not patented). The new cultivar was discovered as a single plant within this population of plants of the cultivar 'Remembrance' and was distinguished by its bi-colored leaves compared to the solid green leaves of the cultivar 'Remembrance'.

Asexual propagation of the new cultivar at Pijnacker, The Netherlands, has shown that the unique features of this new Guzmania plant are stable and reproduced true to type in successive generations of asexual propagation.

The new Guzmania has not been observed under all possible environmental conditions. The phenotype may vary somewhat with variations in environment such as temperature and light intensity, without, however, any variance in genotype. The following observations, measurements and comparisons describe plants grown in Pijnacker, The Netherlands, in 13-cm containers in a glass greenhouse with average day and night temperatures of 20C.

The following traits have been repeatedly observed and are determined to be the unique characteristics of 'Sunstar'. These characteristics in combination distinguish 'Sunstar' as a new and distinct cultivar:

1. Young leaves that have green margins with dark pink centers.

2. Mature leaves that have green margins with light yellow centers.

The accompanying colored photograph illustrates the overall appearance of the new cultivar, showing the colors as true as it is reasonably possible to obtain in colored reproductions of this type.

The photograph comprises a side perspective view of a typical potted plant of 'Sunstar'.

Actual colors may appear slightly different from the colors in the photograph due to light reflectance.

In the following description, color references are made to The Royal Horticultural Society Colour Chart except where general terms of ordinary dictionary significance are used.

Botanical classification: Guzmania cultivar 'Sunstar'.

Parentage: Naturally occurring mutation of the cultivar 'Remembrance' (not patented).

Propagation: By divisions.

Plant description:

*Plant shape.*—Upright, inverted triangle, symmetrical.

*Growth habit.*—Erect when young, becoming outwardly arching as leaves develop. Appropriate for 10 to 20-cm containers.

*Plant height.*—50 to 60 cm from soil level to top of leaf plane.

*Plant vigor.*—Moderately vigorous.

*Crop time.*—15 to 18 months are usually require from planting of a young plant to a finished 13-cm container.

*Rooting habit.*—Central tap root.

*Rooting time.*—About 30 days at a temperature of 22C.

*Foliage description.*—Quantity: 16 to 20 per 13-cm plant. Leaf shape: Linear, sword-like. Leaf length: 50 to 60 cm. Leaf width: 2.5 to 3.5 cm. Margin: Entire. Leaf tip: Acute. Leaf texture: Leathery, smooth, glabrous. Leaf color: Young foliage, upper surface: Margin: 137A. Center: 47D. Young foliage, lower surface: Margin: Slightly paler than 137A. Center: Close to 47D. Mature foliage, upper surface: Margin: 137B. Center: 10D. Mature foliage, lower surface: Margin: Slightly paler than 137B. Center: Slightly paler than 10D.

Flower description:

*Flower appearance.*—Similar to plants of the cultivar Remembrance, no other differences. Showy bright red bracts with yellow inner floral bracts subtending the flowers.

*Flower arrangement.*—Inflorescences of 10 to 40 single bell-shaped flowers. Plants flower yearround.

*Flower longevity.*—Inflorescences may continue to flower for 3 to 4 months, individual flowers last about 2 days. Flowers persistent.

*Flower diameter.*—About 5 mm.

*Flower depth (height).*—About 1 cm.

*Flower color.*—Yellow, 10A to 13B.

*Calyx.*—Shape: Funnel. Size: 4 to 12 cm.

*Stamens.*—Quantity: 6. Anther shape: Cylindrical. Anther size: About 3.5 mm.

*Pistils.*—Style length: About 1.5 cm.

Disease resistance: No resistance or susceptibility to diseases has been noted under commercial production conditions.

It is claimed:

1. A new and distinct cultivar of Guzmania plant named 'Sunstar', as illustrated and described.

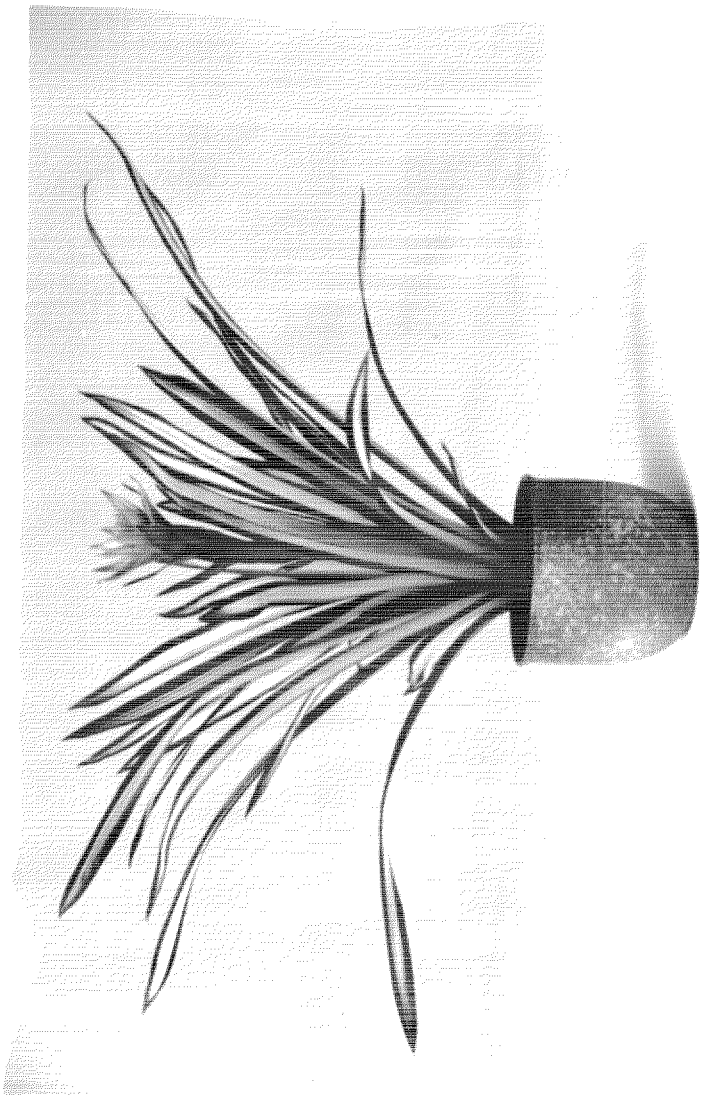

* * * * *